Figure 3:
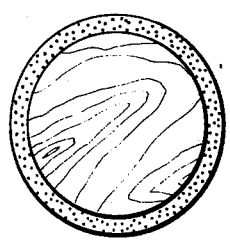

United States Patent [19]
Jennings, Sr.

[11] 3,956,951
[45] May 18, 1976

[54] METHOD OF SHAVING

[76] Inventor: Joseph W. Jennings, Sr., Box 208, Star Rte. 1, Spring Branch, Tex. 78070

[22] Filed: May 8, 1974

[21] Appl. No.: 468,097

[52] U.S. Cl. .................................. 83/14; 83/22; 424/73
[51] Int. Cl.² .......................................... B26D 7/08
[58] Field of Search ............. 83/14, 22, 13; 424/73

[56] References Cited
UNITED STATES PATENTS
3,811,349  5/1974  Jennings ........................... 83/22 X
3,862,310  1/1975  Quasius ............................. 424/73 X Primary Examiner—Frank T. Yost

[57] ABSTRACT

A method of shaving which comprises the steps of rubbing the wet skin surface with a solid mass of a solvent-free, selected water soluble, high molecular weight polymer and thereafter, passing a blade-type razor over the skin to shave off unwanted hair.

4 Claims, 3 Drawing Figures

METHOD OF SHAVING

BACKGROUND OF THE INVENTION

The search for a more efficient and satisfactory method of removing unwanted hair from the human body is a continuing endeavor and razors for that purpose, with specific claims of improved performance, are being constantly offered to the market.

A parallel endeavor is the development of preshave preparations to help alleviate the detrimental skin abrasion and after-shave irritation often associated with the shaving procedure. Within about the past decade, advances have been made and U.S. Patents granted on Methods of Shaving which employ soapless, non-foaming preshave preparations to facilitate the passage of the razor blade over the skin surface and protect the skin from the abrading action of the razor edge. Those new types of preshave preparations have been based, primarily, on formulations incorporating, as the active ingredient, selected high molecular weight, water soluble polymers.

Those new-type preshave preparations are of two basic physical types. One is in the form of a fluid, aqueous solution of a water-soluble polymer and the other, a solid aqueous solution of a water-soluble polymer. The solid aqueous solution type of preshave preparation apparently demonstrates some performance superiority over the liquid aqueous solution type, as it can be placed, on the skin surface, in a higher concentration of polymer molecules than with the fluid aqueous solution formulation with a resultant increased ability to guard the skin surface against the abrading action of the razor edge.

The solid aqueous solution type preshave preparation also has a distinct advantage over the fluid solution type and aerosol foam type preshave preparations, in that, for an equivalent number of shaves, it can be packaged in a container of many units less, both in package size and weight.

The novel and unique feature, of the invention of my Method of Shaving, is primarily, concerned with the physical aspects of the device employed to create a superior protective film on the skin to effectively aid passage of the razor over the skin and guard the skin surface against the nicking and abrading action of the razor edge.

That device, quite simply, consists of a solid, solvent-free mass of selected size and shape of a suitable, high molecular weight, water soluble polymer with such mass having attached a suitable handle or grip to facilitate manual manipulation of the device. The polymer portion, of the device, is preferably a comparatively thin wafer with preferably, a round plan form but which may also be of oval, rectangular, square or other plan form. The wafer thickness is determined by the number of shaves to be secured from a single device.

It is calculated that a polymer wafer of about 1⅜ inch diameter, a thickness of about ⅛ inch and 2 gm weight will yield daily shaves for about 2 months. This device, having a polymer wafer of the foregoing dimension and a suitable handle, will be no more than 1⅜ inch diameter, 1½ inch in height and weight only about 10 grams.

The preferred water soluble polymer, for use in the fabrication of the device used with my Method of Shaving, is polyethylene oxide having a molecular weight of about 4,000,000. That material is normally supplied as a white, dry powder.

The polymer has been easily formed into a solid, solvent-free wafer by pressing the powdered material into a cavity with the desired plan configuration. The resulting wafer is of a relatively hard, dense structure which will withstand normal handling and usage.

In commercial production, the wafer can be quickly formed, at minimum cost, in a pharmaceutical tableting machine. The fabrication, of this unique shaving device, is completed by attaching it to the handle with contact-type cement or other suitable adhesive.

Figure 2:
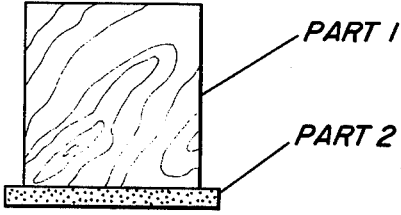
Figure 1:
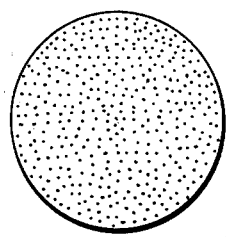

FIG. 1, FIG. 2 and FIG. 3, on the attached drawing show respectively the bottom plan view, the elevation view and the top plan view of the assembled device. On FIG. 2 are indicated the handle portion, Part 1 of the device, which can be made of plastic, cork, wood or other suitable material and Part 2, the polymer wafer portion of the device.

The preferred procedure with my Method of Shaving follows:

1. Wash face with soap and water
2. Rinse all soap from face and leave skin wet
3. Place polymer wafer against skin and vigorously rub area to be shaved with the shave device until a drag or stickiness becomes apparent (this will require only about 45 seconds)
4. Shave off unwanted hair with blade-type razor (if at any time, the polymer film tends to become dry or tacky, simply rub wet fingertips over skin and film will regain full efficiency without degredation or removal)
5. Preferably, wipe face with damp cloth and allow to dry, or rinse face and dry after shaving (the residual preparation, remaining on the skin, is a very excellent skin conditioner)

Because the polymer wafer part, of the shaving device, contains no adulterating solvent, the result of rubbing it onto the wet skin is to create, on the skin, an unusually dense, tough layer of polymolecular fibers which gives unsurpassed protection against razor abrasion.

Other advantages derived from the unique device, used in my Method of Shaving, follow:

From the marketing standpoint, the device can be produced at a comparatively low cost with minimum investment in time and equipment. Because this device requires no permanent envelope package such as a plastic bottle or pushup type container or steel can, the single most costly item in production of most of other preshave preparations, cost will be greatly reduced.

Compared to other preshave preparations, my device will have an infinitely long shelf life.

Because of its comparatively small size and extemely light weight, my shaving device is much less costly to ship, store and display. Its small size and weight make it most attractive to travelers.

The device makes possible the saving of appreciable quantities of valuable, scarce raw materials, now required in the packaging of competetive products and reduces disposal of empty containers.

The invention claimed is:

1. A Method of Shaving which comprises the steps of rubbing the wetted skin with a solid, solvent-free mass of selected shape and size of a suitable, high molecular weight, water soluble polymer and thereafter, shaving off unwanted hair with a blade type razor.

2. A Method, according to claim 1, where the water soluble polymer is polyethylene oxide.

3. A Method, according to claim 1, where the water-soluble polymer has a molecular weight of about 4,000,000.

4. A Method, according to claim 1, where the solid mass of solvent-free, water soluble polymer is attached to a grip or handle to facilitate manipulation of the mass.

* * * * *